United States Patent [19]

Oka et al.

[11] 4,248,889

[45] Feb. 3, 1981

[54] 3,5-DIHYDROXYPENTANOIC ESTER DERIVATIVES HAVING ANTIHYPERLIPAEMIC ACTIVITY

[75] Inventors: Hidehiko Oka; Akira Terahara; Akira Endo, all of Tokyo, Japan

[73] Assignee: Sankyo Company Limited, Tokyo, Japan

[21] Appl. No.: 88,619

[22] Filed: Oct. 26, 1979

[30] Foreign Application Priority Data

Oct. 30, 1978 [JP] Japan ............................. 53-133407

[51] Int. Cl.³ .................. A61K 31/215; C07C 69/732
[52] U.S. Cl. .................................... 424/308; 560/56; 560/60
[58] Field of Search ...................... 560/60, 56; 24/308

[56] References Cited

U.S. PATENT DOCUMENTS 2,915,532  12/1959  Walton .................................. 560/60
4,007,217   2/1977  Kogure et al. ........................ 560/60

Primary Examiner—Joseph E. Evans

Attorney, Agent, or Firm—Frishauf, Holtz, Goodman & Woodward

[57] ABSTRACT

3,5-Dihydroxypentanoic ester derivatives of formula (I):

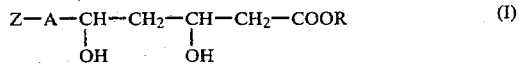

$$Z-A-CH-CH_2-CH-CH_2-COOR \qquad (I)$$
$$\phantom{Z-A-}|\phantom{CH-CH_2-}|$$
$$\phantom{Z-A-}OH\phantom{CH_2-}OH$$

wherein:
A represents an alkylene group which is optionally substituted by one or more alkyl groups, or an alkenylene group;
Z represents a substituted or unsubstituted aryl or aryloxy group; and
R represents a $C_1$–$C_4$ alkyl group) may be prepared by reacting a dianion of an acetoacetic ester with an aldehyde of formula Z-A-CHO (wherein A and Z are as defined above) and then reducing the resulting compound. These 3,5-dihydroxypentanoic ester derivatives have antihyperlipaemic activity and are thus valuable pharmaceuticals.

28 Claims, No Drawings

3,5-DIHYDROXYPENTANOIC ESTER DERIVATIVES HAVING ANTIHYPERLIPAEMIC ACTIVITY

BACKGROUND TO THE INVENTION

The present invention relates to a series of new 3,5-dihydroxypentanoic ester derivatives, to their preparation and to their use as antihyperlipaemic agents.

It is currently believed that a causitive factor in diseases such as atherosclerosis and hyperlipaemia is the deposition of cholesterol in the body, particularly within the arteries. A number of compounds are available for reducing the deposition of cholesterol, including clofibrate and simfibrate. Also, our U.S. Patent Application Ser. No. 576,651, filed May 12, 1975, now U.S. Pat. No. 3,983,140, discloses a series of compounds (designated ML-236A, ML-236B and ML-236C) which are 4-hydroxy-2-pyrone derivatives. There is, however, a continuing need for new compounds having this activity.

BRIEF SUMMARY OF INVENTION

The present invention provides a series of new 3,5-dihydroxypentanoic ester derivatives of formula (I):

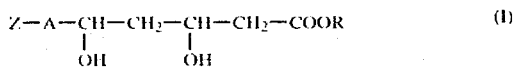

wherein:
A represents an alkylene group optionally having one or more alkyl substituents, or an alkenylene group;
Z represents a substituted or unsubstituted aryl or aryloxy group; and
R represents a $C_1$-$C_4$ alkyl group.

The invention also provides a method of preparing the 3,5-dihydroxypentanoic ester derivatives of formula (I) which comprises reacting a dianion of an acetoacetic ester with an aldehyde of formula (II):

(wherein A and Z are as defined above), and then reducing the resulting compound to form said 3,5-dihydroxypentanoic ester derivative of formula (I).

The invention still further provides a pharmaceutical preparation comprising, as active ingredient, a 3,5-dihydroxypentanoic ester derivative of formula (I) together with a pharmaceutically acceptable carrier or excipient.

DETAILED DESCRIPTION OF INVENTION

In the above compounds, where A represents an alkylene group optionally substituted by a alkyl group, it is preferably a $C_1$ or $C_2$ alkylene group optionally substituted with a $C_1$-$C_3$ alkyl group. Preferred examples of such groups represented by A are the methylene, ethylene, methylethylene and dimethylmethylene groups. Where A represents an alkenylene group, this is preferably a $C_2$ or $C_3$ alkenylene group and most preferably a vinylene group or a propenylene group.

Where Z represents an aryl group, this is preferably a phenyl group, a naphthyl group or a tetrahydronaphthyl (e.g. 5,6,7,8-tetrahydro-1-naphthyl) group. Where the aryl group is substituted, the substituents are preferably one or more halogen atoms and/or $C_1$-$C_3$ alkyl groups, preferably chlorine atoms or methyl groups. Preferred examples of such substituted aryl groups are o-chlorophenyl, m-chlorophenyl, p-chlorophenyl, 2,4-dichlorophenyl, 3,5-dichlorophenyl, 2,6-dichlorophenyl, 2-methyl-1-naphthyl, and 2-methyl-5,6,7,8-tetrahydro-1-naphthyl groups. Where Z represents an aryloxy group, this is preferably a phenoxy group or a naphthoxy group. Where the aryloxy group is substituted, the substituents are preferably one or more halogen, particularly chlorine atoms. Preferred substituted aryloxy groups are o-chlorophenoxy, m-chlorophenoxy, p-chlorophenoxy, 2,4-dichlorophenoxy, 3,5-dichlorophenoxy and 2,6-dichlorophenoxy groups.

R represents an alkyl group having from 1 to 4 carbon atoms, preferably a methyl, ethyl or propyl group and most preferably an ethyl group.

Representative examples of compounds of formula (I) are given below. The compounds are hereafter identified by the numbers assigned to them in the following list:

1. Ethyl 3,5-dihydroxy-7-phenylheptanoate.
2. Ethyl 7-p-chlorophenyl-3,5-dihydroxyheptanoate.
3. Ethyl 3,5-dihydroxy-7-(1-naphthyl)heptanoate.
4. Ethyl 3,5-dihydroxy-7-(2-methyl-1-naphthyl)heptanoate.
5. Ethyl 3,5-dihydroxy-7-(2-methyl-5,6,7,8-tetrahydro-1-naphthyl)heptanoate.
6. Ethyl 3,5-dihydroxy-8-(1-naphthyl)octanoate.
7. Ethyl 3,5-dihydroxy-8-(2-methyl-1-naphthyl)octanoate.
8. Ethyl 3,5-dihydroxy-7-phenylhept-6-enoate.
9. Ethyl 3,5-dihydroxy-6-phenoxyheptanoate.
10. Ethyl 6-(o-chlorophenoxy)-3,5-dihydroxyhexanoate.
11. Ethyl 7-(2,6-dimethyl-1-naphthyl)-3,5-dihydroxyheptanoate.
12. Ethyl 3,5-dihydroxy-7-(o-methylphenyl)heptanoate.
13. Ethyl 7-(2,6-dimethylphenyl)-3,5-dihydroxyheptanoate.
14. Ethyl 7-(o-chlorophenyl)-3,5-dihydroxyheptanoate.
15. Ethyl 7-(2,6-dichlorophenyl)-3,5-dihydroxyheptanoate.

The 3,5-dihydroxypentanoic ester derivatives of formula (I) may be prepared by reacting a dianion of an acetoacetic ester with an aldehyde of formula (II):

(wherein Z and A are as defined above). The dianion may be prepared from the acetoacetic ester by known means.

This reaction may be summarized by the following reaction scheme:

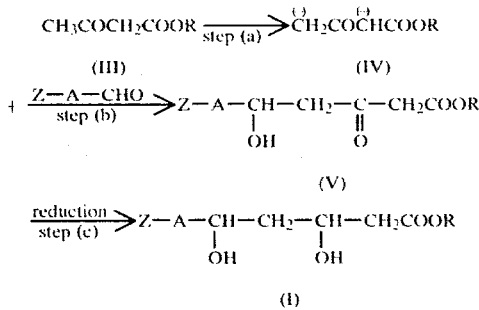

Step (a)

The conversion of the acetoacetic ester (III) to danion (IV) may be effected by adding sodium hydride or metallic sodium in an anhydrous aprotic polar solvent to a solution of the acetoacetic ester (III) in an anhydrous aprotic polar solvent, under ice-cooling, stirring the resulting mixture, usually at a temperature of from $-5°$ C. to $-10°$ C., for 30–60 minutes, and then adding an alkyllithium (e.g. n-butyllithium), an aryllithium (e.g. phenyllithium), potassium t-butoxide or lithium diisopropylamide thereto. Examples of suitable aprotic polar solvents are diethyl ether, diisopropyl ether, diisobutyl ether, dioxan and tetrahydrofuran, of which tetrahydrofuran is preferred. It is customary and preferred to use the acetoacetic ester (III) and the other reagents in equimolar amounts.

Alternatively, this reaction may be carried out using one mole of the acetoacetic ester (III) and 2 moles of the alkyllithium, aryllithium, potassium t-butoxide or lithium diisopropylamide, but without employing the sodium hydride or metallic sodium.

The acetoacetic ester dianion (IV) thus formed in situ may be employed as such in the subsequent reaction without intermediate isolation or purification.

Step (b)

The conversion of the acetoacetic ester dianion (IV) to the compound (V) is effected by adding the aldehyde Z-A-CHO, with ice-cooling, to a reaction mixture containing the dianion (IV) after stirring for a while with cooling. The reaction mixture is then stirred for a short time and then the whole mixture is poured into ice-water and acidified with a mineral acid (e.g. hydrochloric or sulphuric acid), thereby forming the desired compound of formula (V). This compound may be recovered from the reaction mixture by conventional means, for example by extracting with a suitable organic solvent (e.g. ethyl acetate), drying over anhydrous sodium sulphate and then evaporating off the solvent under reduced pressure. The isolated product may, if desired, be further purified by conventional means, for example by silica gel column chromatography eluted with a mixture of benzene and ethyl acetate.

Step (c)

The conversion of the compound of formula (V) to the 3,5-dihydroxypentanoic ester (I) may be effected by reducing the compound (V), e.g. with sodium borohydride in an absolute alcohol (e.g. methanol or ethanol) under ice-cooling and then treating the reaction mixture with a mineral acid (e.g. hydrochloric acid or sulphuric acid). After completion of the reaction, the 3,5-dihydroxypentanoic ester (I) may be recovered by conventional means, for example by extracting the reaction mixture with a suitable organic solvent (e.g. ethyl acetate), drying the extract over anhydrous sodium sulphate and then evaporating off the solvent under reduced pressure. The isolated product may be further purified by conventional means, for example by silica gel column chromatography eluted with a mixture of benzene and ethyl acetate.

Although intermediate isolation and purification of the compound of formula (V) is desirable, it is not essential and, if desired, step (c) of the process may be effected without first separating or purifying the compound of formula (V).

The biological activity of compounds of the invention was demonstrated by the following test.

Crude enzyme extracted from rat liver was reacted with radioactive acetic acid at 37° C. for 60 minutes. The radioactive cholesterol thus biosynthesized was saponified and precipitated with digitonin, and the radioactivity was measured to determine the amount of cholesterol produced. The reaction was repeated, by adding one of the compounds of the invention listed in the following Table at the beginning of the reaction, and the amount of cholesterol biosynthesized was again determined, to give a quantitative measurement of the inhibitory effect of the compounds of the invention. The concentrations ($\mu$g/ml) of the compounds of the invention and of a known compound (clofibrate) which gave approximately 50% inhibition of cholesterol biosynthesis re reported in the following Table as $I_{50}$ values [see Bricker et al, The Journal of Biological Chemistry, 247, 4914 (1972)]. The compounds of the invention are identified in the following Table by the numbers heretofore assigned to them.

TABLE

| Compound No. | $I_{50}$ ($\mu$g/ml) |
| --- | --- |
| 1 | 3.7 |
| 2 | 17.2 |
| 3 | 5.0 |
| 4 | 0.24 |
| 5 | 1.56 |
| 6 | 3.4 |
| 7 | 1.2 |
| 8 | 9.0 |
| 9 | 23–50 |
| 10 | 5–15.2 |
| Clofibrate | 250–300 |

The foregoing results demonstrate that the compounds of the invention are potent inhibitors of cholesterol biosynthesis and have low toxicity. They are, therefore useful as pharmaceuticals for the treatment of such diseases as hyperlipaemia.

The compounds of the invention can be administered orally by intravenous injection or by any other conventional means and they are preferably formulated with carriers or diluents, e.g. as is well-known for known antihyperlipaemic agents such as chofibrate or simfibrate. The posology is dependent upon the age, body weight and condition of the patient, but the daily dosage for adults is generally from 200 to 3,000 mg/day, more preferably about 1,500 mg/day, conveniently administered in divided doses three or four times a day.

The pharmaceutical preparation of the invention is desirably provided in a form suitable for adsorption in the gastrointestinal tract. Tablets and capsules for oral administration are normally in unit dosage form and contain conventional vehicles, for example: binding agents, such as syrup, gum arabic, gelatin, sorbit, gum tragacanth or polyvinylpyrrolidone; excipients, such as lactose, sucrose, corn starch, calcium phosphate, sorbitol or glycine; lubricants, such as magnesium stearate, talc, polyethylene glycol or silica; disintegrating agents, such as potato starch; or wetting agents, such as sodium lauryl sulphate. Tablets may be coated by any method well-known in the art. Liquid preparations for oral administration may be in the form of aqueous or oily suspensions, solutions, syrups, elixirs or the like or they may be in dried form for redissolution in water or another suitable vehicle. Such liquid preparations may comprise conventional additives, for example suspending agents, such as sorbit syrup, methylcellulose, glucose/sugar syrup, gelatin, hydroxyethylcellulose, carboxymethylcellulose, aluminium stearate gel or a hydrogenated edible fat; emulsifying agents, such as lecithin, sorbitan monoleate or gum arabic; nonaqueous vehicles, such as almond oil, fractionated coconut oil, oily esters, propylene glycol or ethanol; or preservatives, such as methyl p-hydroxybenzoate, propyl p-hydroxybenzoate or sorbic acid.

Injectable preparations are preferably provided in the form of unit dosage ampoules or in multiple dosage vessels with added preservatives. These preparations may be in the form of suspensions, solutions or emulsions in oily or aqueous vehicles and may also comprise conventional additives, for example suspending agents and/or stabilizers and/or dispersing agents (such as those exemplified above). Alternatively, the active ingredient may be in the form of a powder which can be redissolved in a suitable vehicle, e.g. pyrogen-free sterilized water, at the time of use.

The pharmaceutical preparations of the invention preferably contain not less than 0.1% by weight, more preferably from 10 to 60% by weight, of the active ingredient, depending upon the route of administration. A unit dosage form of the preparation preferably contains from 50 to 500 mg of the active ingredient.

The invention is further illustrated by the following Examples, which describe the preparation of certain of the compounds of the invention.

EXAMPLE 1

Ethyl 3,5-dihydroxy-7-(1-naphthyl)heptanoate (Compound No. 3)

(a) A solution of 5.2 g (0.04 mole) of ethyl acetoacetate in a small quantity of anhydrous tetrahydrofuran was added dropwise to 1.2 g (0.04 mole) of sodium hydride (in the form of a 55% w/w suspension in oil) in 100 ml of anhydrious tetrahydrofuran, with ice-cooling and stirring. The mixture was then stirred for 30 minutes, after which it was cooled to a temperature of from $-10°$ C. to $-5°$ C. To the mixture were added dropwise 30 ml of an n-hexane solution containing 0.04 mole of n-butyllithium. The mixture was stirred at a temperature from 5° C. to 0° C. for 30 minutes, after which it was cooled to $-60°$ C. 6 g (0.033 mole) of 3-(1-naphthyl)propionaldehyde in 50 ml of anhydrous tetrahydrofuran were then added all at once to the reaction mixture. After stirring the mixture for 30 minutes, it was poured into about 500 ml of ice-water. It was then acidified by the addition of hydrochloric acid, with stirring, and the tetrahyrofuran layer was separated. The aqueous layer was extracted three times, each time with 100 ml of ethyl acetate. The tetrahydrofuran layer and the ethyl acetate extracts were combined, washed with saturated aqueous sodium chloride and dried over anhydrous sodium sulphate. The solvent was then evaporated off under reduced pressure. The resulting residue was adsorbed on a silica gel column chromatography and the fractions eluted with a 10:3 by volume mixture of ethyl acetate and n-hexane were evaporated to dryness to give 4.0 g (yield 30%) of ethyl 5-hydroxy-7-(1-naphthyl)-3-oxoheptanoate.

(b) 4.0 g (0.013 mole) of ethyl 5-hydroxy-7-(1-naphthyl)3-oxoheptanoate, prepared as described in step (a) above, dissolved in a small quanity of anhydrous ethanol were added dropwise to 0.57 g (0.015 mole) of sodium borohydride in 20 ml of absolute ethanol, with ice-cooling and stirring. When the addition was complete, cooling was immediately stopped and the mixture was allowed to warm to room temperature and was stirred for 30 minutes. After adding 200 ml of water, the mixture was acidified by the addition of sulphuric acid, saturated with sodium chloride and extracted three times, each with 50 ml of ethyl acetate. The combined extracts were washed with saturated aqueous sodium chloride and dried over anhydrous sodium sulphate. The solvent was then evaporated off under reduced pressure and the resulting residue was adsorbed on a silica gel column chromatograph. The fractions eluted with a 9:1 by volume mixture of benzene and ethyl acetate were concentrated to dryness to give 2.4 g (yield 23%) of the desired Compound No. 3 in the form of a colourless oil.
$n_D^{21} = 1.15615$.

Thin layer chromatography (silica gel, developed with a 1:1 by volume mixture of benzene and ethyl acetate) $R_f$ value=0.53.

Elemental Analysis: Calculated for $C_{19}H_{24}O_4$: C, 72.12%; H, 7.65%. Found: C, 71.97%; H, 8.05%.

Nuclear Magnetic Resonance Spectrum (CDCl$_3$) $\delta$ ppm: 1.15 (triplet, 3H, J=6 cps, —OCH$_2$C$\underline{H}_3$); 1.4–2.1 (multiplet, 4H, H$_2$ at 6- and 4-positions); 2.45 (doublet, 2H, J=8 cps, H$_2$ at 2-position); 2.9–3.4 (multiplet, 2H, CH$_2$ at 7-position); 4.05 (quartet, 2H, J=6 cps, —OC$\underline{H}_2$CH$_3$); 3.5–4.5 (multiplet, 6H, H and OH at 3- and 5-positions); 7.2–8.15 (multiplet, 7H, naphthyl).

Infrared Absorption Spectrum (Nujol-Trade Mark) $\nu_{max}$ cm$^{-1}$: 1735 (C=O), 3400 (OH).

EXAMPLE 2

Ethyl 3,5-dihydroxy-6-phenoxyheptanoate (Compound No. 9)

(a) 13 g (0.1 mole) of ethyl acetoacetate in 30 ml of anhydrous tetrahydrofuran were added drop by drop to a 50% w/w suspension in oil of 4.8 g (0.1 mole) of sodium hydride in 100 ml anhydrous tetrahydrofuran, with ice-cooling and stirring. The mixture was stirred for a further 30 minutes and then cooled to a temperature from $-10°$ C. to $-5°$ C. To the mixture was added dropwise 70 ml of an n-hexane solution containing 0.1 mole of n-butyllithium. The mixture was stirred at a temperature from $-5°$ C. to 0° C. for 30 minutes to produce the dianion of ethyl acetoacetate and was then cooled to $-40°$ C.

9 g (0.06 mole) of 2-phenoxypropionaldehyde in 30 ml of anhydrous tetrahydrofuran were added all at once to the reaction mixture. After stirring for 30 minutes, the whole reaction mixture was poured into about 1 liter of ice-water. The resulting mixture was acidified by the addition of sulphuric acid and then extracted three times, each time with 200 ml of ethyl acetate. The combined extracts were dried over anhydrous sodium sulphate and then the solvent was evaporated off under reduced pressure. The resulting residue was adsorbed on a silica gel chromatography column and eluted with a 98:2 by volume mixture of benzene and ethyl acetate, to give 5.7 g (yield 33.9%) of ethyl 5-hydroxy-3-oxo-6-phenoxyheptanoate, in the form of an oil.

(b) To 2.5 g (0.006 mole) sodium borohydride in 30 ml of absolute ethanol was added dropwise 30 ml of an absolute ethanol solution containing 3.5 g 80.0135 mole) of the ethyl 5-hydroxy-3-oxo-6-phenoxyheptanoate obtained in step (a). After completion of the addition, cooling was immediately stopped and the mixture was allowed to warm to room temperature and was stirred for about 40 minutes. To the reaction mixture were then added about 300 ml of ice-water and the mixture was then acidified by the addition of 2 N sulphuric acid. After saturating the solution with sodium chloride, it was extracted three times, each time with 50 ml of ethyl acetate. The combined extracts were dried over anhydrous sodium sulphate and then the solvent was evaporated off, to give 1.3 g (yield 37%) of ethyl 3,5-dihydroxy-6-phenoxyheptanoate.

The compound was obtained in the form of a colourless oil having an $R_f$ value on thin layer chromatography (silica gel, developed with a 2:1 by volume mixture of benzene and ethyl acetate) of 0.6.

Following the procedures described in Examples 1 and 2, the following compounds were also obtained:

Compound No. 1

Ethyl 3,5-dihydroxy-7-phenylheptanoate

Colourless oil, $R_f$ value (thin layer chromatography, silica gel, developed with 3:2 by volume n-hexane and ethyl acetate)=0.3.

Compound No. 2

Ethyl 7-p-chlorophenyl-3,5-dihydroxyheptanoate

Colourless oil, $R_f$ value (thin layer chromatography, silica gel, developed 3:2 by volume n-hexane and ethyl acetate)=0.33.

Compound No. 4

Ethyl 3,5-dihydroxy-7-(2-methyl-1-naphthyl)heptanoate

Colourless oil, $n_D^{21}=1.570$, $R_f$ value (thin layer chromatography, silica gel, developed with 1:1 by volume benzene and ethyl acetate)=0.55.

Compound No. 5

Ethyl 3,5-dihydroxy-7-(2-methyl-5,6,7,8-tetrahydro-1-naphthyl)heptanoate

Colourless oil, $R_f$ value (thin layer chromatography, silica gel, developed with 3:1 by volume benzene and ethyl acetate)=0.3

Compound No. 6

Ethyl 3,5-dihydroxy-8-(1-naphthyl)octanoate

Colourless oil, $R_f$ value (thin layer chromatography, silica gel, developed with 3:1 by volume benzene and ethyl acetate)=0.33.

Compound No. 7

Ethyl 3,5-dihydroxy-8-(2-methyl-1-naphthyl)octanoate

Colourless oil, $R_f$ value (thin layer chromatography, silica gel, developed with 3:1 by volume benzene and ethyl acetate)=0.33.

Compound No. 8

Ethyl 3,5-dihydroxy-7-phenylhept-6-enoate

Colourless oil, $R_f$ value (thin layer chromatography, silica gel, developed with 1:1 by volume benzene and ethyl acetate)=0.49.

Compound No. 10

Ethyl 6-(o-chlorophenoxy)-3,5-dihydroxyhexonoate

Colourless oil, $R_f$ value (thin layer chromatography, silica gel, developed with 3:2 by volume n-hexane and acetone)=0.38.

We claim:

1. 3,5-Dihydroxypentanoic ester derivatives of formula (I):

$$Z-A-\underset{OH}{CH}-CH_2-\underset{OH}{CH}-CH_2-COOR \qquad (I)$$

wherein:
A represents an alkylene group an alkylene group having one or more alkyl substituents, or an alkenylene group;
Z represents a halo or alkyl substituted or unsubstituted aryl or aryloxy group; and
R represents a $C_1$-$C_4$ alkyl group.

2. Compounds as claimed in claim 1, wherein A represents a $C_1$ or $C_2$ alkylene group optionally substituted with a $C_1$-$C_3$ alkyl group.

3. Compounds as claimed in claim 2, wherein A represents a methylene, ethylene, methylethylene or dimethylmethylene group.

4. Compounds as claimed in claim 1, wherein A represents a $C_2$ or $C_3$ alkylene group.

5. Compounds as claimed in claim 4, wherein A represents a vinylene or propenylene group.

6. Compounds as claimed in claim 1, wherein Z represents a phenyl group, a naphthyl group or a tetrahydronaphthyl group optionally substituted by a halogen atom or a $C_1$-$C_3$ alkyl group.

7. Compounds as claimed in claim 6, wherein Z represents a phenyl, naphthyl or tetrahydronaphthyl group optionally substituted with a chlorine atom or a methyl group.

8. Compounds as claimed in claim 7, wherein Z represents an o-chlorophenyl, m-chlorophenyl, p-chlorophenyl, 2,4-dichlorophenyl, 3,5-dichlorophenyl, 2,6-dichlorophenyl, 2-methyl-1-naphthyl, or 2-methyl-5,6,7,8-tetrahydro-1-naphthyl group.

9. Compounds as claimed in claim 1, wherein Z represents a phenoxy group or a naphthoxy group optionally substituted with a halogen atom.

10. Compounds as claimed in claim 9 wherein Z represents a o-chlorophenoxy, m-chlorophenoxy, p-chlorophenoxy, 2,4-dichlorophenoxy, 3,5-dichlorophenoxy or 2,6-dichlorophenoxy group.

11. Ethyl, 3,5-dihydroxy-7-phenylheptanoate of the formula of claim 1.

12. Ethyl 7-p-chlorophenyl-3,5-dihydroxyheptaoate of the formula of claim 1.

13. Ethyl 3,5-dihydroxy-7-(1-naphthyl)heptanoate of the formula of claim 1.

14. Ethyl 3,5-dihydroxy-7-(2-methyl-1-naphthyl)heptanoate of the formula of claim 1.

15. Ethyl 3,5-dihydroxy-7-(2-methyl-5,6,7,8-tetrahydro-1-naphthyl)heptanoate of the formula of claim 1.

16. Ethyl 3,5-dihydroxy-8-(1naphthyl) octanoate of the formula of claim 1.

17. Ethyl 3,5-dihydroxy-8-(2-methyl-1-naphthyl)octanoate of the formula of claim 1.

18. Ethyl 3,5-dihydroxy-7-phenylpent-6-enoate of the formula of claim 1.

19. Ethyl 3,5-dihydroxy-6-phenoxyheptanoate of the formula of claim 1.

20. Ethyl 6-(o-chlorophenoxy)-3,5-dihydroxyhexanoate of the formula of claim 1.

21. Ethyl 7-(2,6-dimethyl-1-naphthyl)-3,5-dihydroxyheptanoate of the formula of claim 1.

22. Ethyl 3,5-dihydroxy-7-(o-methylphenyl)heptanoate of the formula of claim 1.

23. Ethyl 7-(2,6-dimethylphenyl)-3,5-dihydroxyheptanoate of the formula of claim 1.

24. Ethyl 7-(o-chlorophenyl)-3,5-dihydroxyheptanoate of the formula of claim 1.

25. Ethyl 7-(2,6-dichlorophenyl)-3,5-dihydroxyheptanoate of the formula of claim 1.

26. A pharmaceutical preparation comprising as active ingredient, a 3,5-dihydroxypentanoic ester derivative of formula (I):

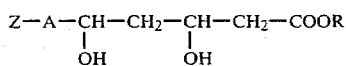

(wherein:

A represents an alkylene group, an alkylene group having one or more alkyl substituents, or an alkenylene group;

Z represents a halo or alkyl substituted or unsubstituted aryl or aryloxy group; and R represents a $C_1$–$C_4$ alkyl group), together with a pharmaceutically acceptable carrier or excipient.

27. A pharmaceutical preparation as claimed in claim 26, in a form suitable for oral or parenteral administration.

28. A pharmaceutical preparation as claimed in claim 26, wherein said 3,5-dihydroxypentanoic ester derivative is selected from the group consisting of:

Ethyl 3,5-dihydroxy-7-phenylheptanoate;
Ethyl 7-p-chlorophenyl-3,5-dihydroxyheptanoate;
Ethyl 3,5-dihydroxy-7-(1-naphthyl)heptanoate;
Ethyl 3,5-dihydroxy-7-(2-methyl-1-naphthyl)heptanoate;
Ethyl 3,5-dihydroxy-7-(2-methyl-5,6,7,8-tetrahydro-1-naphthyl)heptanoate;
Ethyl 3,5-dihydroxy-8-(1-naphthyl)octanoate;
Ethyl 3,5-dihydroxy-8-(2-methyl-1-naphthyl)octanoate;
Ethyl 3,5-dihydroxy-7-phenylhept-6-enoate;
Ethyl 3,5-dihydroxy-6-phenoxyheptanoate; and
Ethyl 6-(o-chlorophenoxy)-3,5-dihydroxyhexanoate.

* * * * *